United States Patent
Haddadi

(10) Patent No.: US 9,723,982 B2
(45) Date of Patent: Aug. 8, 2017

(54) METHOD FOR DETERMINING THE DOMINANT EYE

(75) Inventor: Ahmed Haddadi, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 564 days.

(21) Appl. No.: 14/001,743

(22) PCT Filed: Mar. 5, 2012

(86) PCT No.: PCT/FR2012/050452
§ 371 (c)(1),
(2), (4) Date: Nov. 27, 2013

(87) PCT Pub. No.: WO2012/123658
PCT Pub. Date: Sep. 20, 2012

(65) Prior Publication Data
US 2014/0098343 A1    Apr. 10, 2014

(30) Foreign Application Priority Data

Mar. 11, 2011  (FR) ...................... 11 52004

(51) Int. Cl.
*A61B 3/14*  (2006.01)
*A61B 3/113*  (2006.01)
(Continued)

(52) U.S. Cl.
CPC .............. *A61B 3/14* (2013.01); *A61B 3/0066* (2013.01); *A61B 3/0091* (2013.01); *A61B 3/113* (2013.01); *A61B 3/145* (2013.01); *A61B 3/18* (2013.01)

(58) Field of Classification Search
CPC A61B 3/14; A61B 3/145; A61B 3/113; A61B 3/0033; A61B 3/0058;
(Continued)

(56) References Cited

U.S. PATENT DOCUMENTS 1,515,305 A * 11/1924 Hartinger .................. A61B 3/00
351/205
1,712,847 A * 5/1929 Ritholz ..................... A61B 3/02
351/222
(Continued)

FOREIGN PATENT DOCUMENTS

EP  WO2010118292  10/2010

OTHER PUBLICATIONS

Search Report dated Oct. 2011, re French document No. 1152004.

*Primary Examiner* — Jordan Schwartz
(74) *Attorney, Agent, or Firm* — Young & Thompson

(57) ABSTRACT

A method is provided for determining the dominant eye of a person using equipment designed to acquire at least one image of the face of the person, then process the image, and finally return information enabling the person to know which eye is the dominant eye thereof. The method uses a sighting device that is identifiable and locatable in relation to the equipment, with the viewing being carried out through a window with both eyes open. The size of the window is such that it does not allow the person to see said target with both eyes at the same time. The equipment acquires at least one image for viewing the position of both eyes of the person, processing the image by performing calculations while taking into account the position of a central point located between both eyes, the position of the target and the position of the window.

15 Claims, 2 Drawing Sheets

(51) Int. Cl.
*A61B 3/18* (2006.01)
*A61B 3/00* (2006.01)

(58) Field of Classification Search
CPC ... A61B 3/0066; A61B 3/0075; A61B 3/0091; A61B 3/08; A61B 3/18
USPC .................................................. 351/239–240
See application file for complete search history.

(56) References Cited

U.S. PATENT DOCUMENTS

| | | | | |
|---|---|---|---|---|
| 1,747,844 | A * | 2/1930 | Ritholz | A61B 3/02 351/222 |
| 4,595,203 | A * | 6/1986 | DeLano | A63F 3/0625 273/148 R |
| 5,016,282 | A | 5/1991 | Tomono et al. | |
| 5,481,622 | A | 1/1996 | Gerhardt et al. | |
| 5,555,895 | A * | 9/1996 | Ulmer | A61B 3/113 351/210 |
| 5,689,619 | A | 11/1997 | Smyth | |
| 6,636,296 | B1 * | 10/2003 | Faulkner | G01C 3/22 33/277 |
| 2002/0082100 | A1 * | 6/2002 | Moore | A63B 63/08 473/160 |
| 2011/0109880 | A1 | 5/2011 | Nummela | |
| 2013/0314668 | A1 * | 11/2013 | Haddadi | A61B 3/111 351/204 |
| 2013/0321774 | A1 * | 12/2013 | Van Dalen | A61B 3/02 351/221 |
| 2014/0016090 | A1 * | 1/2014 | Bonnin | A61B 3/113 351/204 |
| 2014/0085608 | A1 * | 3/2014 | Clopton | A61B 3/113 351/209 |

* cited by examiner

METHOD FOR DETERMINING THE DOMINANT EYE

RELATED APPLICATIONS

This application is a National Phase Application of PCT/FR2012/050452, filed on Mar. 5, 2012, which in turn claims the benefit of priority from French Patent Application No. 11 52004 filed on Mar. 11, 2011, the entirety of which are incorporated herein by reference.

BACKGROUND

Field of the Invention

The invention relates to a method for determining the dominant eye of an individual. The dominant eye of an individual is the eye that directs alignment of the 2 eyes, in other words it is the eye that directs the movement and fixation of the other eye during certain operations such as, for example, sighting. It is therefore important, especially for an optician, to be able to ascertain the dominant eye of an individual who needs to wear spectacles.

Description of Relate Art

Methods for determining the dominant eye of an individual already exist. These methods commonly require individuals to subject themselves to long and constraining visual tests consisting in looking at an object through an aperture produced in a sheet, and/or in carrying out sighting operations that involve blocking vision from one eye, then the other. In the end it is the individual themselves who, based on their own observations during these tests, will deduce which of their eyes is their dominant eye. An optician may also determine this dominant eye by observing the eyes of the individual during testing, or by analyzing the orientation of certain objects that the individual might use during said tests.

The methods for determining the dominant eye of an individual according to the invention limit the constraints placed on said individual, especially by allowing them to keep both eyes open during the testing. In addition, they implement a step consisting in delivering, to said person, the result of the test in an attractive and indisputable form that requires not the least bit of interpretation. Finally, the result is delivered almost instantaneously, in the continuity of the test, without a waiting period. The methods according to the invention provide a certain level of comfort, and also possess a demonstrative character.

The invention relates to a method for determining the dominant eye of an individual, comprising the following steps:
  positioning the individual in front of an apparatus designed to acquire at least one frontal image of said individual, then to process said image and lastly to reconstruct information allowing the individual to ascertain their dominant eye;
  viewing, by means of a sighting device equipped with an optical window, a target that is identifiable and discernible relative to the apparatus, this viewing being carried out through said window and with both eyes open, the dimensions of said window being such that they do not allow the individual to see said target with both eyes at the same time;
  acquiring, using the apparatus, at least one image allowing at least the position of the two eyes of the individual to be seen;
  calculationally processing said at least one image, the calculations taking into account the position of a central point located between the two eyes, the position of the target and the position of the window; and
  reconstructing, using the apparatus, the information indicating the dominant eye of the individual.

OBJECTS AND SUMMARY

The principle behind a method according to the invention consists in capturing at least one image of the individual looking at the target through the sighting device, in processing this image, then in reconstructing information relating to their dominant eye directly to the individual. Thus, the method is rapid, complete and demonstrative because it delivers indisputable information to the individual in the continuity of the test. In addition, this method is user-friendly in nature because it allows the individual to take center stage while keeping both eyes open throughout. The information delivered by the apparatus may be conveyed to the individual in various forms. Specifically, it may either be visual information, contained in an image on a screen or on a piece of paper, revealing the dominant eye by means of a distinct sign, or audible information conveyed by means of a pre-recorded voice clearly announcing the dominant eye of the individual. The apparatus may either employ a camera or a camcorder. The apparatus may either be moveable and be moved during the method in order to acquire at least one image, or be fixed and take the form, for example, of a column that also includes image processing means and means for reconstructing said image. The individual may take the test while standing or while sitting. In the case where the individual is sat down, the seat may be fixed, setting, precisely and repeatably, the position of the individual relative to the apparatus. The target is fixed and the location where it is installed may be easily located. It is generally located in the immediate environment of the apparatus, so that by placing themselves in front of said apparatus, the individual can perceive it directly, without turning their head. The sighting device may, for example, be formed by an immovable part, placed on the ground, in a carefully selected location between the individual and the apparatus. The optical window is a local element in the sighting device, through which the person may look at the target, said window being dimensioned so that the person may see the target only with one eye. The images delivered by the apparatus must be sufficiently precise for the processing means to be able to pinpoint a central point located between the two eyes of the individual, and the position of the optical window.

Preferably, the sighting device is portable, the individual manually adjusting the position of this device in order to see the target. The sighting device is sufficiently light and small for the individual to be able to easily manipulate it by hand, without having to make any particular effort. In this configuration, the individual positions the sighting device to their liking, in a position in which they can comfortably see the target. Generally, the individual places the sighting device a few tens of centimeters, preferably between 30 cm and 60 cm, from their eyes, as they would to read a book.

Advantageously, the means for acquiring the image is a camcorder. This means is preferred because its use is flexible, and because it permits a multiplicity of zoomed-out or zoomed-in shots to be taken continuously. In addition, this means delivers images that are particularly adapted to the processing employed by the method.

In a first preferred embodiment of a method according to the invention, both eyes of the individual and the optical window appear simultaneously in a given image. In this configuration, it is assumed that the means for acquiring the image possess a good enough resolution to be able to precisely pinpoint the various elements required for the calculational processing of said image, such as the optical window of the sighting device, and the point located between the two eyes of the individual.

In a second preferred embodiment of a method according to the invention, the apparatus acquires at least two images, a first image that is a zoomed-out view in which both the eyes of the individual and the optical window feature at the same time, and a second image that is a zoomed-in view of the eyes of the individual and that allows the position of a central point located between the eyes to be precisely identified, the processing of the first image being carried out on the basis of information gathered from the second image. Often, the resolution of the means for acquiring the image is insufficient to allow the position of the various elements required for the calculational processing to be pinpointed on a given image. In this case, a zoomed-in view of the eyes of the individual may be taken allowing a central point located between said eyes to be precisely pinpointed. Once this pinpointing operation has been carried out, this zoomed-in view is combined with the first image in which both the eyes of the individual and the position of the optical window of the sighting device appear at the same time.

Preferably, the individual wears a pair of spectacles, to which a clip equipped with at least one marker is fastened, at least one of the markers being intended to pinpoint a central point between the eyes. Specifically, in order to aid with the pinpointing of a central point located between the eyes of the individual, an artificial marker may be used, allowing said central point to be pinpointed more easily. Generally, this marker is identifiable by its shape and/or its color. Other lateral markers may be used, especially in order to pinpoint, precisely, the position of each eye. Employing a clip makes it possible to create a reference point linked to the head. Such a clip is, for example, described in patent application US 2009/0262302.

Advantageously, the calculational processing is based on the position of a first straight line joining the target and the optical window, and a second straight line connecting said target to a central point located between the two eyes of the individual, said positions being determined relative to a reference straight line passing through the target and lying parallel to the sighting axis of the means for acquiring the image. The precision with which these straight lines can be positioned depends on how precisely the optical window and the central point between the two eyes can be pinpointed. If the target and the means for acquiring the image are aligned along a vertical axis, then the reference straight line and the sighting axis of said acquiring means coincide.

More precisely, the calculational processing comprises at least two steps, the first of which consists in determining a first angle between the first straight line and the reference straight line, and a second angle between the second straight line and said reference straight line, and the second step in which consists in comparing said angles to each other.

Preferably, the apparatus employs a display screen to deliver a processed image on which appears, overlaid, at least one identifier indicating the dominant eye of the individual. This way of reconstructing the information allows the individual to see themselves in an image embellished with information allowing their dominant eye to be identified. The identifier is a line or a mark, which may take a number of shapes, sizes or colors, unambiguously indicating the dominant eye of the individual.

Advantageously, the identifier is a line joining the dominant eye of the individual to the optical window of the sighting device. In video mode, the images may, for example, be selected and/or reconstructed to form an augmented reality film, in which the moving face of the individual appears with the line moving at the same time as the dominant eye.

Preferably, the sighting device is equipped with at least one pinpointing marker, at least one of which allows the position of the optical window to be identified. In this way, whatever the position of the sighting device at the moment when the individual views the target through the optical window, the position of the optical window will always be visible on the image. Other lateral markers may also be affixed to said device, in order to pinpoint its orientation on the image.

Advantageously, the optical window is a through-orifice. This is the simplest version, the most rapid to implement and the least expensive. In other preferred embodiments, this optical window may take the form of a thickness of transparent glass or plastic, said glass or said plastic possibly being tinted. Likewise, this optical window may be entirely or partially obstructed by a sliding obstructing member, allowing the dimensions of this window to be adapted depending on the circumstances.

Preferably, the apparatus is a fixed column, the target being placed on said column. In this way, the elements required to implement the method according to the invention are all grouped together and the method may then be carried out in a smaller space.

The invention also relates to a portable sighting device for implementing a method according to the invention. The principal feature of a sighting device according to the invention is that it comprises a thin board comprising an optical window, the dimensions of said board being compatible with easy manual manipulation, the board comprising a base possessing at least one marker representing the position of the optical window in order to allow said window to be pinpointed on an image in the case where the board is inclined.

Advantageously, the optical window is dimensioned so that an individual cannot see the target with both eyes at the same time, the board partially covering their view cone, the base of which is bounded by the two eyes of the individual and the tip of which corresponds to the target.

The methods for determining the dominant eye of a person according to the invention have the advantage of being complete because, in addition to providing a simple and rapid test that has few constraints, they comprise a final step consisting in conveying, to the person, the result of the test in a precise visual form. In addition, the methods according to the invention are advantageous in two respects, on the one hand because the individual takes center stage in front of a camcorder, if required placing a clip on their spectacles, and on the other hand because they are able to see themselves, on a screen or a paper printout, with the indication of their dominant eye. Lastly, these methods are safe, reliable and perfectly repeatable.

BRIEF DESCRIPTION OF THE DRAWINGS

A description of a preferred embodiment of a method for determining the dominant eye according to the invention is given below with reference to FIGS. 1 to 4, in which:

FIG. 2b is a perspective front view of the device in FIG. 2a;

DETAILED DESCRIPTION

Figure 1:
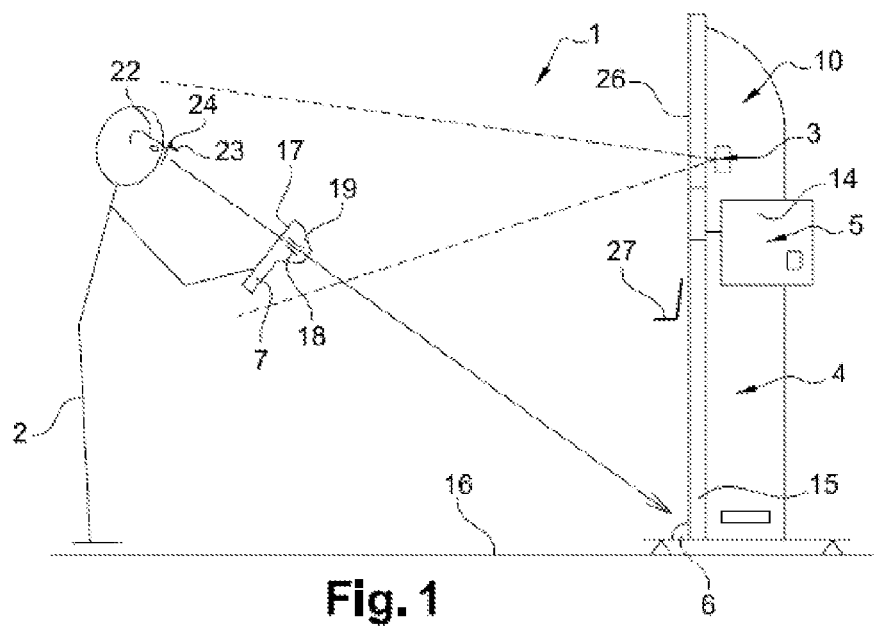
FIG. 1 is a side view of an installation provided for applying the method according to the invention, and showing an individual in the process of viewing a target through a portable sighting device.
Figure 3A:
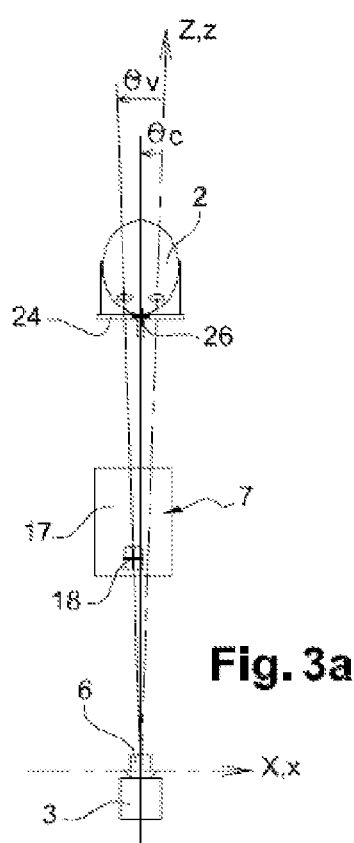
FIG. 3a is a top view of the installation in FIG. 1, and showing the person in the process of viewing a target through a board, the target being placed plumb with an acquiring camcorder.
Figure 3B:
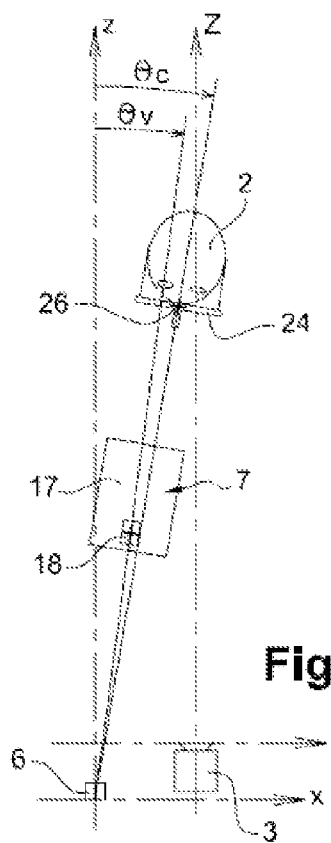
FIG. 3b is a top view of the installation in FIG. 1, and showing the person in the process of viewing a target through a board, the target being horizontally offset relative to an acquiring camcorder.

With reference to FIGS. 1, 3a and 3b, an installation 1 allowing a method for determining the dominant eye of an individual 2 according to the invention to be applied, employs an apparatus 10 equipped with: a camcorder 3 allowing at least one image 13 to be acquired, means 4 allowing said image 13 to be processed, and means 5 allowing said processed image 13 to be reconstructed; a system for illuminating said individual 2; a physical and fixed target 6 the position of which is perfectly identified and discernible; a portable sighting device 7 held in the hand of the individual 2; and various markers 20, 21, 23, 26 allowing the position of the sighting device 7 and of each eye of the individual 2 to be pinpointed on the photo or film furnished by the camcorder 3. The apparatus takes the form of a fixed vertical column 10 incorporating the camcorder 3, the height of which is adjustable depending on the height of the individual 2 taking the test. Ideally, the height of the camcorder 3 is positioned at approximately the same height as the eyes of the individual 2. The means 4 for processing the image 13 comprise an electronic component and an information processing component, especially allowing a colored line 11 to be overlaid on the photo 13 or film acquired by the camcorder 3, this line 11 being generated on the basis of the position of a central point 26 located between the eyes of the individual 2, of the position of the sighting device 7, and of the position of the target 6, said line 11 thus directly indicating the dominant eye 12 of the individual 2. The means 5 for reconstructing the processed image 13 comprise a display screen 14 that may either be directly incorporated into the column 10, or connected to the latter via appropriate cables. Advantageously, the screen 14 is turned toward the individual so that they can view their own image 13 directly, and discover, almost instantaneously, and without moving, which of their eyes is their dominant eye 12. The target 6 consists of a visible reference point that may take any sort of form, and it is positioned in the lower part 15 of the column 10, on an imaginary vertical axis of symmetry separating said column 10 into two equal halves. The individual 2 may take the test for detecting their dominant eye 12 according to the invention while standing or sitting. If they are standing, the target 6 is placed at a height about 70 cm from the ground 16. If they are sat down, the target 6 is placed level with the ground 16. Preferably, the camcorder 3 is positioned in the column 10 in such a way that said vertical axis also splits it into two symmetrical halves, so that said camcorder 3 and said target 6 are perfectly plumb with each other and perfectly aligned along said vertical axis. The individual 2 who wishes to ascertain which of their eyes is their dominant eye 12, picks up the sighting device 7 in order to view the target 6 therethrough. The column 10 comprises a half-silvered mirror 26 concealing the camcorder 3 and allowing the person 2 to position themselves correctly in front of said column 10, by reference to their own image reflected by said mirror 26, in order to take the test under the right conditions. The column 10 also comprises a protruding holder 27, for holding the sighting device 7 when the latter is not being used.

Figure 2A:
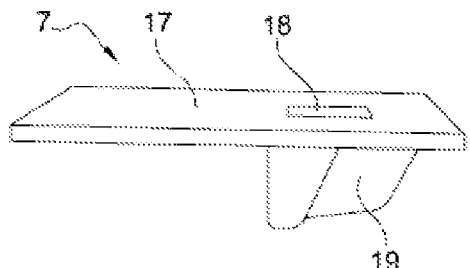
FIG. 2a is a perspective side view of a portable sighting device used to implement a method according to the invention.
Figure 2B:
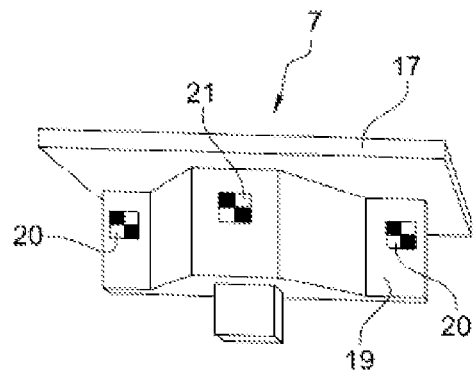

With reference to FIGS. 2a and 2b, a portable sighting device 7 capable of being used in the context of the method according to the invention takes the form of a rectangular board 17, preferably 20 cm by 30 cm in area, having a thickness smaller than 5 cm, and equipped with an optical window 18, said board 17 comprising a base 19 on which three markers 20, are fixed allowing the position of said board 17 to be pinpointed on a photo 13 or a film, two markers 20 having lateral positions and the other marker 21 having a central position on the device 7. Each marker 20, 21 consists of a square divided into four identical small squares, two of which squares, arranged on a diagonal, are white in color, the other two squares being black in color. Advantageously, to improve detection as a function of ambient light, and in order to prevent saturation, these markers 20, 21 may be light gray and dark gray in tone. The central marker 21 represents the position of the optical window 18 in the board 17. Specifically, when the individual 2 is in the process of viewing the target 6 through the sighting device 7, they will have a tendency to incline the latter, with the risk that the optical window 18 will disappear from the photo 13 or the film taken by the camcorder 3. Since the calculational processing of the photo 13 or film is in part based on the position of this optical window 18, it is important to be able to pinpoint it precisely, whatever the inclination of said sighting device 7. The central marker 21 is positioned on the base 19 in order to meet this need. The two lateral markers 20 contribute to pinpointing the orientation of the sighting device 7. The optical window 18 is an element located in the sighting device 7, and through which the individual 2 will view the target 6. This optical window 18 preferably takes the form of a hole produced in the board 17 and passing through the latter, but may also consist of a thickness of a transparent material such as a glass or plastic, this material possibly being tinted. Likewise, the dimensions of this optical window 18 may be adjustable, by way of, for example, a sliding obstructing element integrated into the board 17. In order to be used in the context of a method according to the invention, the optical window 18 must be dimensioned in such a way that the person cannot see the target 6 through this window 18 with both eyes at the same time. The individual positions themselves about 1.5 m from the camcorder and places the sighting device 7 at an observation distance between 30 and 60 cm, the aperture of the hole 18 having a length or a diameter between 20 and 30 mm. Thus, the position of the window 18 relative to the individual 2 will be such that only the dominant eye 12 will be able to observe the target 6, even if the image 13 of the scene is integrated by the visual system 3. Therefore, this leads to the optical window 18 being located laterally relative to the dominant eye 12.

Preferably, in the context of a measurement at an opticians, the individual 2 wears a frame 22 containing corrective glasses. Since the principal of the method relies on the acquisition of an image 13 processed on the basis of the precise identification of the position of a central point located between the eyes, of the position of the optical window 18 in the board 17, and of the position of the target 6, it is therefore important to be able to rigorously pinpoint the position of said central point and, if required, each eye. To do this, the spectacles 22 are equipped with markers 23, 26, two 23 of which are located at the edge of the frame, and the third 26 of which is located in line with a central point located between the eyes. These three markers 23, 26 are supported by a bar 24 that can be clip-fastened to the frame of said spectacles 22, in a substantially horizontal position, above each glass, this clip possibly, for example, being analogous to that described in patent application US 2009/0262302. The markers 23, 26 affixed to the frame 22 may be analogous to those 20, 21 of the sighting board 17, but may also take other forms that are more adapted to fitting to a pair of spectacles 22. Clip-fastening is preferred in order to increase the flexibility, rapidity and attractiveness of a method according to the invention. The system for illuminating the individual 2 is a conventional system that is securely fastened to the column 10 forming the apparatus, this illuminating system being intended to accentuate contrasts in a photo or a film, in order to better pinpoint certain elements of the face of the individual 2, such as, for example, the various markers 23, 26.

With reference to FIGS. 3a and 3b, the calculational processing of the image 13 requires the position of the marker 26 located between the two eyes of the individual 2, the position of the optical window 18 or the marker 21 allowing it to be identified, and the position of the target 6, to be pinpointed. Although the positions of the central point 26 and the optical window 18 can be pinpointed via the camcorder, in contrast this is not the case for the target 6, which does not appear in the images 13. It is therefore essential for the coordinates of the target 6 to be correctly identified in order to process said images. FIG. 3a illustrates a perfectly symmetric configuration, in which the target 6 and the camcorder 3 are strictly aligned along a vertical axis. FIG. 3b illustrates an asymmetric configuration in which the target 6 and the camcorder 3 are horizontally offset. In both configurations (X, Z) is a coordinate system located in a horizontal plane and having as its origin a reference point located on the lens of the camcorder 3. The Z axis marks the sight axis of said camcorder, and the X axis is an axis perpendicular to this sight axis Z.

The angle $\theta v$ is the angle formed between the straight line parallel to the Z axis passing through the center of the target 6, and the straight line passing through the center of the target 6 and the optical window 18 of the sighting device 7.

The angle $\theta c$ is the angle formed between the straight line parallel to the Z axis passing through the center of the target 6 and the straight line passing through the marker 26 of the clip 24 marking a central point located between the two eyes.

The angles $\theta v$ and $\theta c$ are measured in the clockwise direction.

Under these conditions:
if $\theta v > \theta c$, the dominant eye is the right eye; and
if $\theta v < \theta c$, the dominant eye is the left eye.
$\theta v$ and $\theta c$ are calculated using the coordinates, in the plane (x, z), x lying parallel to X and z lying parallel to Z, the origin of this coordinate system (x, z) being a central point of the target 6,
of the center of the optical window 18 (xv, zv);
of the marker 26 representing a central point located between the eyes of the individual 2 (xc, zc); and
of the center of the target 6 (xr, zr).
Thus, it is easy to deduce the following relationships:

$$\theta v = \arctan((zv-zr)/(xv-xr))$$

$$\theta c = \arctan((zc-zr)/(xc-xr))$$

Figure 4:
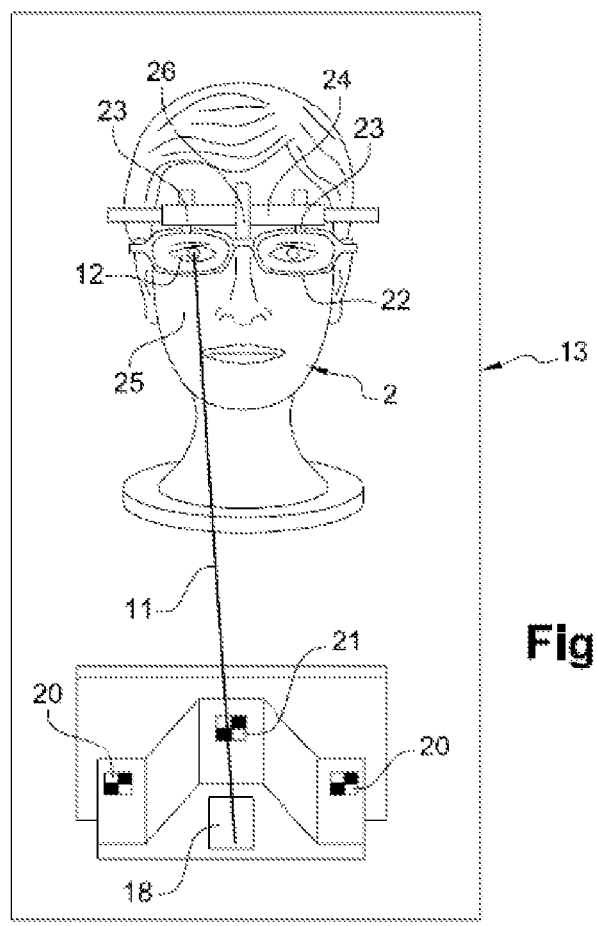
FIG. 4 is a view of the final image provided by the method according to the invention, and showing a person viewing a target through a board, said image being embellished with an overlaid line indicating the dominant eye of said person.

With reference to FIG. 4, the processed image 13 delivered by the column 10 is a photo in which the face 25 of the individual 2 wearing spectacles 22 equipped with the bar 24 fitted with the markers 23, 26, and the sighting device 7 also fitted with its visible markers 20, 21, can be viewed. The processing of the image 13 consists, in a first step, in pinpointing the position of the marker 26 representing a central point located between the two eyes, and that of the marker 21 representing the optical window 14, then, in order to demonstrate to the individual their sight direction, in overlaying, on the photo 13, a straight colored line 11 joining the dominant eye 12 to the central marker 21 of the sighting device 7, the central marker 21 representing the position of the optical window 18.

A method according to the invention implements the following steps:
a step of fastening the clip 24, 23, 26 to the spectacles 22 of the individual 2 in order to allow a central point 26 between the eyes to be pinpointed on a photo 13 or a film;
a step of positioning the individual 2 in front of the acquiring column 10, at a distance of about 1.3 m, with reference to the image of the individual 2 reflected in the mirror 26;
a step in which the individual 2 acquires the sighting device 7 equipped with its optical window 18;
a step in which the individual 2 adjusts to their liking the position of the sighting device 7, and then looks at the target 6 through the optical window 18 while keeping both eyes open;
a step in which the camcorder 3 is triggered and then paused on an image 13 in order to freeze the face 25 of the individual 2 and the position of the sighting device 7;
a step of processing said image 13; and
a step in which a processed image 13 is reconstructed on the screen 14, on which image a straight colored line 11, joining the dominant eye 12 of the individual 2 to the central marker 21 of the sighting device 7, is overlaid, said marker 21 representing the optical window 18.

The method may also implement a final step consisting in printing, onto paper, the image 13 in which the face 25 of the individual 2 and the colored line indicating their dominant eye 12 appear.

The method according to the invention may make provision for the sequential addition of masks covering one eye then the other, and for the lateral movement of the optical window 18 to be observed using a sequence of acquired images 13.

The invention is not limited to the various embodiments described above, which are given by way of nonlimiting example.

The invention claimed is:
1. A method for determining the dominant eye of an individual, comprising the following steps:
positioning the individual in front of an apparatus designed to acquire at least one frontal image of said individual, then to process said image and lastly to reconstruct information allowing the individual to ascertain their dominant eye;

viewing, by means of a sighting device equipped with an optical window, a target that is identifiable and discernible relative to the apparatus, this viewing being carried out through said window and with both eyes open, the dimensions of said window being such that they do not allow the individual to see said target with both eyes at the same time;

acquiring, using the apparatus, at least one image, or at least a first and second image, wherein said at least one image, or together, said at least first and second image, provide imaging of at least the position of the two eyes of the individual and of the optical window to be seen;

calculationally processing said at least one image, or said at least a first and second image, the calculations taking into account the position of a central point located between the two eyes of the individual, the position of the target and the position of the window; and reconstructing, using the apparatus, the information indicating the dominant eye of the individual, said information being derived from the calculational processing.

2. The method as claimed in claim 1, wherein the sighting device is portable, and in that the individual manually adjusts the position of this device in order to see the target.

3. The method as claimed in claim 1, wherein the means for acquiring the image is a camcorder.

4. The method as claimed in claim 1, wherein both eyes of the individual and the optical window appear simultaneously in a given image.

5. The method as claimed in claim 1, wherein the apparatus acquires at least two images, a first image that is a zoomed-out view in which both the eyes of the individual and the optical window feature at the same time, and a second image that is a zoomed-in view of the eyes of the individual and that allows the position of a central point located between the eyes to be precisely identified, the processing of the first image being carried out on the basis of information gathered from the second image.

6. The method as claimed in claim 1, wherein the individual wears a pair of spectacles, to which a clip equipped with at least one marker is fastened, at least one of the markers being intended to pinpoint a central point between the eyes.

7. The method as claimed in claim 1, wherein the calculational processing is based on the position of a first straight line joining the target and the window, and a second straight line connecting said target to a central point located between the two eyes, said positions being determined relative to a reference straight line passing through the target and lying parallel to the sighting axis of the means (3) for acquiring the image.

8. The method as claimed in claim 7, wherein the calculational processing has at least two steps, the first of which is determining a first angle ($\theta v$) between the first straight line and the reference straight line, and a second angle ($\theta c$) between the second straight line and said reference straight line, and the second of which is comparing said angles to each other.

9. The method as claimed in claim 1, wherein the apparatus employs a display screen to deliver a processed image on which appears, overlaid, on at least one image, at least one identifier indicating the dominant eye of the individual.

10. The method as claimed in claim 9, wherein the identifier is a line joining the dominant eye of the individual to the optical window of the sighting device.

11. The method as claimed in claim 1, wherein the sighting device is equipped with at least one pinpointing marker, at least one of which allows the position of the optical window to be identified.

12. The method as claimed in claim 1, wherein the optical window is a through-orifice.

13. The method as claimed in claim 1, wherein the apparatus is a fixed column, and in that the target is placed on said column.

14. A portable sighting device comprising:
a thin board having an optical window, the dimensions of said board being compatible with easy manual manipulation when held in the hand of an individual, said board having a first face and an opposite, second face;
a base centered on said optical window, said base comprising a protrusion centered on said optical window and extending from the second face of said board, so that an individual holding said board with the first face of said board facing the individual may, when viewing through the optical window, observe an object through said protrusion;
at least one first marker positioned on the protrusion, the at least one first marker representing the position of the optical window; and
at least two lateral markers positioned on the protrusion, a first of the at least two lateral markers positioned on a first side of the at least one first marker and a second of the at least two lateral markers positioned on a second side of the at least one first marker, the at least two lateral markers positioned on the protrusion to assist in pinpointing the orientation of the sighting device, in order to allow said optical window to be pinpointed on a target image in the case where the board is inclined, wherein,
positioning the individual in front of the first face of the board allows acquiring at least one frontal image of the individual,
with the individual holding the board with the first face of the board facing the individual and the individual viewing through the optical window and observing the object through the protrusion, the object being a target that is identifiable and discernible relative to the sighting device, this viewing being carried out through said optical window and with both eyes open, the dimensions of said optical window being such that they do not allow the individual to see said target with both eyes at the same time, allows acquiring, using an apparatus, at least one image, or at least a first and second image, wherein said at least one image, or together, said at least first and second image, provide imaging of at least the position of the two eyes of the individual and of the optical window to be seen, and
the at least one image, or the at least a first and second image allowing calculationally processing that take into account the position of a central point located between the two eyes of the individual, the position of the target and the position of the optical window, and allow reconstructing, using the apparatus, of information indicating the dominant eye of the individual, said information being derived from the calculational processing.

15. The device as claimed in claim 14, wherein that the optical window is adjustable so that the dimension thereof is such that an individual viewing said target images therethrough cannot see said target image with both eyes at the same time, the board partially covering their view cone.

* * * * *